United States Patent
Kramer et al.

[11] Patent Number: 6,103,898
[45] Date of Patent: Aug. 15, 2000

[54] PREPARATION OF CYCLIC UREA DERIVATIVES

[75] Inventors: Andreas Kramer, Freinsheim; Wolfgang Siegel, Limburgerhof, both of Germany

[73] Assignee: BASF Aktiengesellschaft, Ludwigshafen, Germany

[21] Appl. No.: 09/161,368

[22] Filed: Sep. 28, 1998

[30] Foreign Application Priority Data

Oct. 2, 1997 [DE] Germany ............ 197 43 760

[51] Int. Cl.$^7$ ............ C07D 233/34; C07D 233/40; C07D 239/10; C07D 249/02; C07D 243/04

[52] U.S. Cl. ............ 540/460; 540/492; 544/298; 544/302; 544/305; 544/309; 544/310; 544/314; 544/315; 544/318; 548/316.4; 548/316.7; 548/317.5; 548/325.5; 548/326.1

[58] Field of Search ............ 548/316.4, 316.7, 548/317.1, 317.5, 325.5, 326.1; 544/298, 302, 305, 309, 310, 314, 315, 318; 540/460, 492

[56] References Cited

U.S. PATENT DOCUMENTS

| | | | |
|---|---|---|---|
| 2,422,400 | 6/1947 | Farlow | 260/309 |
| 3,079,279 | 2/1963 | Van Loo | 117/139 |
| 3,091,617 | 5/1963 | Burris | 260/309 |
| 3,185,539 | 5/1965 | Madison et al. | 8/116 |
| 4,063,021 | 12/1977 | Cipriani et al. | 548/317 |
| 4,617,400 | 10/1986 | Ito et al. | 548/317 |
| 4,650,877 | 3/1987 | Mabire et al. | 548/319 |
| 4,864,026 | 9/1989 | Bickert et al. | 544/315 |
| 4,897,480 | 1/1990 | Schoenleben | 544/315 |
| 4,925,940 | 5/1990 | Franz et al. | 544/315 |
| 4,970,321 | 11/1990 | Betz et al. | 548/317 |
| 5,428,165 | 6/1995 | Wardle | 544/301 |
| 5,783,706 | 7/1998 | Henkelmann et al. | 548/316 |

FOREIGN PATENT DOCUMENTS

| | | |
|---|---|---|
| 198345 | 10/1986 | European Pat. Off. . |
| 248220 | 12/1987 | European Pat. Off. . |
| 249136 | 12/1987 | European Pat. Off. . |
| 356973 | 3/1990 | European Pat. Off. . |
| 60204728 | 3/1984 | Japan . |
| 1517820 | 7/1978 | United Kingdom . |

OTHER PUBLICATIONS

Bogatsky et al., *Synthesis*, 1982, 464, 465.
Hussain et al., *J. Med. Chem.*, 14/2, 1971, 138–144.
Dehmlow et al., *Synthetic Comm.*, 18/5, 1988, 487–94.
Raja et al., *Synthesis*, 1983, 1032, 1033.
Vail et al., *J. Or. Chem.*, 30, 1965, 2179–2182.

*Primary Examiner*—Mukund J. Shah
*Assistant Examiner*—Bruck Kifle
*Attorney, Agent, or Firm*—Keil & Weinkauf

[57] ABSTRACT

Cyclic urea derivatives of the formula I

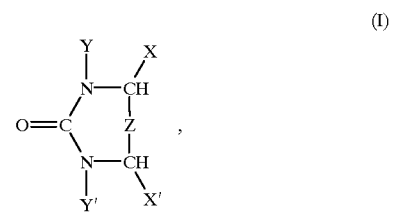

in which X, X', Y, Y' and Z can have various meanings, are prepared by
a) reacting a urea derivative of the formula II

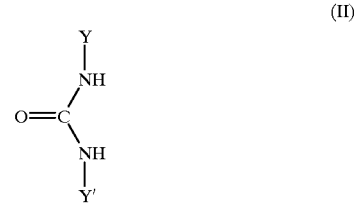

with a diketone of the formula III

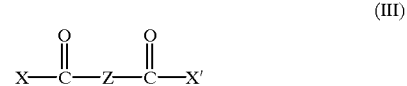

and
b) hydrogenating the product from step a) in the presence of a metal-containing catalyst.

13 Claims, No Drawings

PREPARATION OF CYCLIC UREA DERIVATIVES

The invention relates to a process for preparing cyclic urea derivatives.

Cyclic urea derivatives, especially N,N'-dimethylpropyleneurea (DMPU) and N,N'-dimethylethyleneurea (DMEU), are employed as polar aprotic solvents specifically, for example, in agrochemical and drug syntheses. DMEU or DMPU can be used as solvents to replace the carcinogenic hexamethylphosphoramide (HMPA) especially in reactions in which carbanions or carbanion equivalents are involved.

In addition, many cyclic urea derivatives have pharmacological activity; they influence the central nervous system in particular.

Furthermore, cyclic urea derivatives can also be employed in chemical engineering, eg. in gas scrubbing.

Various processes for preparing cyclic urea derivatives are known:

Bogatsky, A. V. et al. describe, in Synthesis (1982) 464 and 465, the synthesis of cyclic N,N'-dialkylureas by reacting cyclic thioureas with alkyl halides in the presence of aqueous NaOH solution and catalytic amounts of benzyltriethylammonium chloride.

Hussain, M. H. and Lien, E. J., J. Med. Chem. 14/2 (1971) 138–144 disclose the preparation of cyclic ureas by reacting N,N'-dialkylalkylenediamines with urea.

Dehmlow, E. V. and Rao, Y. R. describe, in Synthetic Communications 18/5 (1988) 487–494, the preparation of dimethylethyleneurea (DMEU) and dimethylpropyleneurea (DMPU) by alkylation of the corresponding cyclic ureas with phase-transfer catalysis.

Rajca, A. et al., Synthesis (1983) 1032 and 1033 disclose the preparation of cyclic dialkylurea derivatives by reaction of N,N'-dialkylalkylenediamines with 2-oxo-5-phenyl-1,3,4-oxathiazole or 5-(2,4-dichlorophenyl)-2-oxo-1,3,4-oxathiazole.

EP-A-280 781 and German Priority Application DE-A-37 03 389 on which it is based describe a process for preparing N-alkyl-N'-methylalkyleneureas, especially N,N'-dimethylalkyleneureas, by reacting the corresponding alkyleneureas with formaldehyde to give the N-alkyl-N'-(hydroxymethyl)alkyleneureas, followed by reduction of these compounds to the appropriate N-alkyl-N'-methylalkyleneureas with formic acid.

European Patent Application EP-A-198 345 discloses a process for preparing 1,3-dialkyl-2-imidazolidinones. This entails reacting N,N'-dialkylethylenediamines with urea in the presence of a polar solvent at >180° C.

EP-A-249 136 describes a process for preparing cyclic ureas by reacting an N,N'-dialkylalkylenediamine with urea in a polar solvent at >180° C.

DE-A-25 55 582 discloses a process for preparing acyclic or cyclic ureas by pyrolyzing in each case 2 mol of an appropriate carbamate.

DE-A-26 54 928 discloses a process for preparing N-methylated ureas or alkyleneureas where, starting from ureas or alkyleneureas, the nitrogen atoms are alkylated with formaldehyde in an acid medium in the presence of a hydrogenation catalyst in one step.

GB-B-1 517 820 describes a process for preparing N-methylureas by reacting a urea with formaldehyde in acidic medium and hydrogenating the methylol compound produced in this way on metallic catalysts.

JP-A-60 204728 discloses a reaction of ethyleneurea with alkylating reagents, such as dimethyl sulfate, to give dimethylethyleneurea.

EP-A-248 220 describes a process for preparing cyclic ureas by direct reaction of a diamine with phosgene in the presence of water and an HCl acceptor.

U.S. Pat. No. 4,617,400 describes a process for preparing N,N'-dimethylurea derivatives by reacting a cyclic urea compound with formaldehyde in the presence of hydrogen and a hydrogenation catalyst. The reaction is carried out in the presence of a solid acid.

U.S. Pat. No 2,422,400 describes a process for the catalytic hydrogenation of 1,3-dimethoxymethyl-2-imidazolidinone, 1,3-dihydroxymethyl-2-imidazolidinone or other N,N'-dihydroxymethyl-substituted cyclic ureas. The reaction takes place at 100 to 125° C. in an organic solvent, for example methanol, under a pressure of about 140 bar. The catalyst used is a metallic hydrogenation catalyst, especially a nickel-containing catalyst.

DE-A-44 25 696 discloses a process for preparing 1,3-disubstituted imidazolidinones by reacting ethylene carbonate with at least one compound of the formula $RNH_2$ where R can be H, alkyl, aryl, heteroalkyl or heteroaryl. The reaction is carried out at from 150 to 300° C. under a pressure of about 50 to 150 bar. No solvents or catalysts are employed. A yield of 85% is reported in one example, while the yields are from 42% to 75% in the other 4 examples.

EP-B-356 973 and the German Priority Document DE-A-38 29 848 on which it is based disclose a process for preparing cyclic N,N'-dimethylureas by reacting cyclic alkyleneureas with formaldehyde and excess formic acid, subsequently removing the formic acid still present in the reaction mixture by thermally decomposing it using a catalyst system consisting of a tertiary amine and a copper salt.

DE-A-37 44 120 describes a process for preparing 1,3-dialkyl-2-imidazolidinones by reacting N,N'-dialkylalkylenediamines with carbon dioxide in the gas phase in the presence of catalytic oxides.

Vail, S. L. et al. describe, in J. Org. Chem. 30 (1965) 2179–2182, the formation of condensates from a reaction mixture of dimethylurea and aqueous glyoxal solution at room temperature.

The known processes detailed above are either irrelevant for the industrial scale, involve elaborate reactions, economically unattractive because large amounts of salt are produced, or start from materials which can be obtained only uneconomically.

DE-A-38 00 083 discloses a process for preparing cyclic N,N'-dimethylureas by catalytic hydrogenation of cyclic ureas which have hydroxyl groups in position a to the two nitrogen atoms. Palladium on an inorganic carrier material is used as hydrogenation catalyst. Solvents mentioned as suitable are water and polar organic solvents, for example alcohols. The quoted examples relate, however, only to the preparation of N,N'-dimethylpropyleneurea from N,N'-dimethylolpropyleneurea in aqueous solution. The methylol compound is hydrogenated in the presence of phosphoric acid. The disadvantage of this process is that the reaction mixture must be worked up to remove remaining phosphoric acid. In addition, compounds in which the hydroxyl groups are bonded to ring carbon atoms can be hydrogenated only poorly in this case.

It is an object of the present invention to provide an improved process for preparing cyclic urea derivatives. It was intended in particular to improve the prior art in relation to the starting materials, the reaction procedure and/or the yields.

We have found that this object is achieved by a process for preparing cyclic urea derivatives of the formula I

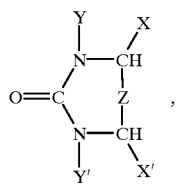

(I)

where
X and X' are, independently of one another, hydrogen, hydroxyl, straight-chain or branched $C_1$–$C_4$-alkyl, $C_3$–$C_{12}$-cycloalkyl, $C_1$–$C_4$-alkoxy or unsubstituted or $C_1$–$C_4$-alkyl-substituted $C_6$–$C_{10}$-aryl;

Y and Y' are, independently of one another, hydrogen, straight-chain or branched $C_1$–$C_4$-alkyl, $C_3$–$C_{12}$-cycloalkyl, or unsubstituted or $C_1$–$C_4$-alkyl-substituted $C_6$–$C_{10}$-aryl, and Z is a single bond or an unsubstituted or X— or X'-substituted $C_1$–$C_4$-alkylene radical, which comprises
a) reacting a urea derivative of the formula II

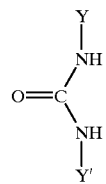

(II)

where Y and Y' have the abovementioned meanings, with a diketone of the formula III

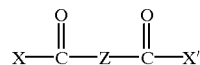

(III)

where X, X' and Z have the abovementioned meanings, and
b) hydrogenating the product from step a) in the presence of a metal-containing catalyst.

The radicals Y and Y' are preferably selected independently of one another from straight-chain or branched $C_1$–$C_4$-alkyl or $C_6$–$C_{10}$-aryl, such as methyl, ethyl, n-propyl, isopropyl, n-butyl, isobutyl or phenyl, especially from methyl or ethyl.

The radicals X and X' are preferably selected independently of one another from hydrogen, hydroxyl, straight-chain or branched $C_1$–$C_4$-alkyl, straight-chain $C_1$–$C_4$-alkoxy or $C_6$–$C_{10}$-aryl. X and X' are particularly preferably hydrogen.

Z is preferably a single bond or a $C_1$–$C_4$-alkylene radical which may be substituted by one or more of the above-defined radicals X or X', particularly preferably methylene, ethylene, propylene or butylene or, especially, a single bond.

The diketone of the formula III may also be employed in the form of its chemical equivalents which liberate the diketone of the formula III under the reaction conditions.

The process according to the invention has the following advantages over the prior art:
Compounds which are substituted in the ring by groups which are to be hydrogenated can be prepared and hydrogenated in high yields.

Compounds of this type can be prepared and hydrogenated continuously, which considerably improves the economics of the process.

Step a) is preferably carried out in aqueous or aqueous/organic solvent. It is particularly preferred to carry out step a) in an aqueous/organic solvent which contains about 1–80% by weight, in particular about 30–60% by weight, of organic solvent based on the precursor mixture. The reaction mixture from step a) is then hydrogenated, where appropriate after further addition of organic solvent.

Another embodiment of the process according to the invention comprises removing the solvent after step a) has been carried out, and taking up the residue in an organic solvent and hydrogenating it.

The aqueous or aqueous/organic solvent can be removed by conventional processes, for example by evaporating off the solvent under reduced pressure.

The cyclic urea derivatives resulting from step a) correspond in particular to formulae IV, V or VI

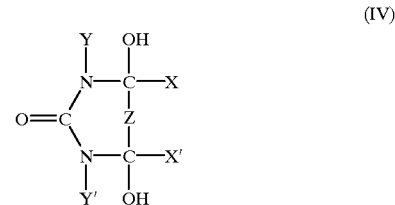

(IV)

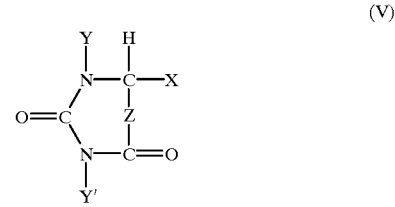

(V)

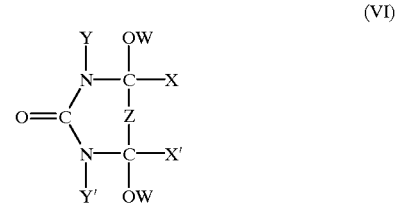

(VI)

where X, X', Y, Y' and Z have the abovementioned meanings, and W is a straight-chain or branched $C_1$–$C_4$-alkyl radical.

The organic solvent preferably used is a $C_1$–$C_6$-alkanol, a $C_1$–$C_5$-carboxylic acid, an ester of a $C_1$–$C_3$-carboxylic acid with a $C_1$–$C_3$-alkanol or a linear or cyclic ether with 3 to 6 members. Particularly preferred organic solvents according to the invention are methanol, ethanol, propanol, isopropanol, butanol, isobutanol, ethyl acetate, dioxane or glacial acetic acid, very particulary preferably methanol.

Step a) can take place in the acidic, neutral or basic range, but preferably at a pH in the range from 3 to 14, particularly preferably 6 to 10. The pH is adjusted with suitable amounts of bases such as KOH, NaOH, alkali metal carbonates, nonnucleophilic amines, salts of aliphatic alcohols or basic ion exchangers, or of acids such as formic acid, sulfuric acid or phosphoric acid, organic sulfonic acids or acidic ion exchangers.

Step a) can be carried out in a conventional pressure-resistant heatable reaction vessel, preferably in aqueous/alcoholic, especially aqueous/methanolic, medium. The reaction temperature and time can vary within a wide range.

The temperature for step a) is generally about 10–100° C., in particular about 20–75° C. The reaction takes from a few minutes to several hours, in particular from about 10 minutes to about 30 hours. The compounds of the formulae II and III are preferably employed in the molar ratio of about 1:1.5 to about 1.5:1.

Step b) is preferably carried out at about 130–300° C., in particular about 150–260° C. The pressure in step b) is preferably about 130–320 bar, in particular about 150–260 bar.

The process according to the invention can be carried out batchwise, semicontinuously or continuously, with a continuous procedure being preferred.

It is possible in principle to employ all hydrogenation catalysts according to the invention. The hydrogenation catalysts particularly employed are oxides of elements in groups Ia to IVa, of groups Ib to VIIIb in the periodic table, and of the lanthanide group or mixtures thereof, and unsupported or supported metal catalysts. Suitable and preferred oxides of elements of groups Ia to IVa of the periodic table are those of lithium, sodium, potassium, calcium, boron, aluminum, silicon and tin, preferably tin, boron and aluminum, especially tin and boron, of group Ib to VIIIb of the periodic table are, for example, those of titanium, zirconium, vanadium, niobium, chromium, molybdenum, manganese, rhenium, cobalt, nickel, ruthenium, rhodium, palladium, osmium, iridium, platinum, copper and silver, preferably nickel, cobalt, ruthenium, palladium, copper or silver, particularly preferably nickel, palladium, copper and silver, and of the lanthanide group are, for example, those of lanthanum, praseodymium, samarium or ytterbium, preferably praseodymium, or mixtures thereof.

Suitable and preferred supported metal catalysts are ruthenium, nickel, rhenium, palladium, platinum, copper, cobalt, rhodium, especially nickel, palladium and rhenium.

The catalysts can be employed as supported catalysts or in compact form, eg. without carrier. Carrier materials which can be used are conventional materials such as pumice, silica, alumina, such as α-, β- or γ-alumina, titanium dioxide, zirconium dioxide, magnesium oxide, silicates, zeolites or carbon in the form of graphite, activated carbon or carbon black, preferably activated carbon, alumina, silica and titanium dioxide, particularly preferably alumina, especially α-alumina. It is also possible to use for preparing the catalysts where appropriate binders and molding aids such as sodium carbonate, potassium carbonate, sodium oxide and magnesium oxide, preferably sodium oxide. The catalyst can be applied to the carrier material for example in a conventional way by impregnating the carrier several times with an aqueous solution of metal salts with intermediate drying, and subsequent conversion of the salts into the oxides. Particularly suitable salts are acetates, carbonates or nitrates. The catalysts can also be employed as fixed bed or in suspension. If required, the catalysts can also be doped with rare earth metals such as scandium, yttrium or cerium. The catalyst is employed according to the invention in an amount of about 1–30%, in particular about 10–30%, of the weight of the product from step a).

The cyclic urea derivatives prepared according to the invention are suitable as aprotic polar solvents for dissolving drugs and high molecular weight substances, especially polyamides, PVC, polystyrene, polyurethanes, polyvinyl alcohol or phenolic resins.

The urea derivatives prepared according to the invention can additionally be used as active ingredient in pharmaceutical compositions, especially in compositions influencing the central nervous system (CNS), preferably in anticonvulsants, antiepileptics, antidepressants, sedatives, relaxants or respiratory stimulants.

The present invention also relates to a cyclic urea derivative of the formula I which can be obtained by the process according to the invention.

The following examples illustrate the invention without, however, restricting it thereto.

EXAMPLES

Example 1

Condensation of N,N'-dimethylurea with glyoxal

1a) Preparation of a compound of the formula IV where X and X' are H, Y and Y' are $CH_3$, and Z is a single bond.

162.9 g of N,N'-dimethylurea are introduced into 268.5 g of 40% strength aqueous glyoxal solution at room temperature (RT). After stirring for 39 min, the pH of the solution is adjusted to 6 to 7, and the water is removed under reduced pressure in a rotary evaporator at 50° C. The residue is taken up in ethanol and dried over sodium sulfate. The ethanol is replaced by acetone and, on cooling to 5° C., 1,3-dimethyl-4,5-dihydroxy-2-imidazolidone (component (1)) precipitates out as a white solid (the yield is more than 60% of theory), which can be hydrogenated to DMEU.

1b) Preparation of a compound of the formula V where X is H, Y and Y' are $CH_3$, and Z is a single bond.

162.9 g of N,N'-dimethylurea are introduced into 268.5 g of 40% strength aqueous glyoxal solution at RT. 188.5 ml of formic acid are added and then the mixture is refluxed for 3 h. The formic acid is subsequently removed at 50° C. under 50 mbar, and the residue is worked up by distillation. The product which distils at 135–140° C. under 20 mbar is 1,3-dimethyl-2,4-imidazolidinedione (component (2)) (N,N'-dimethylhydantoin) in a yield of more than 70% of theory, which can be hydrogenated to DMEU.

1c) The reactants are mixed as in 1a) but no isolation of an intermediate is carried out. The reaction mixture, which contains not only components (1) and (2) but also other higher condensates, is hydrogenated immediately after addition of methanol.

1d) Preparation of a compound of the formula IV where X and X' are H, Y and Y' are $CH_3$, and Z is a single bond.

145 g of a 40% strength aqueous glyoxal solution is adjusted to pH 8 with triethylamine at RT. Then, over the course of 100 min, 88 g of solid dimethylurea are added in portions to the mixture. After 3 h at 20–40° C., the discharge from the reaction is found to contain a yield of 95% of theory of 1,3-dimethyl-4,5-dihydroxyimidazolidone which, after addition of 230 g of methanol, can be hydrogenated without further work-up.

1e) Preparation of a compound of the formula IV where X and X' are H, Y and Y' are $CH_3$, and Z is a single bond.

1728 g of a 40% strength aqueous glyoxal solution are adjusted to pH 9 with 1 molar methanolic sodium methoxide solution at RT. A solution of 880 g of dimethylurea in 880 g of methanol is added dropwise to this mixture. After 1 h at 40° C., the discharge from the reaction is found to contain a yield of 83% of 1,3-dimethyl-4,5-dihydroxyimidazolidone, which can be employed directly for subsequent hydrogenation to DMEU.

Example 2

Hydrogenation of the products described under 1) to DMEU (Preparation of a compound of the formula I where X and X' are H, Y and Y' are $CH_3$, and Z is a single bond.)

10 g of starting material (products from 1 a), b), c), d) and e)) in 100 ml of ethanol are introduced together with 1 to 3 g of catalyst into a 0.3 l autoclave and hydrogenated under 150 to 200 bar of hydrogen at 160 to 200° C. until the pressure is constant. Information on the catalytic metals or oxides employed is given in Table 1.

TABLE 1

| Batch No. | Catalyst | Precursor | Yield |
|---|---|---|---|
| 1 | Raney nickel | from 1a) | 90% |
| | | from 1b) | 87% |
| | | from 1d) | 80% |
| | | from 1e) | 80% |
| 2 | 10.4% Ni; 10.2% Co; 4.2% Cu on $Al_2O_3$ | from 1a) | 83% |
| | | from 1b) | 41% |
| 3 | 50% Ni; 30% Zr; 18% Cu; 1.5% Mo; 0.2% Na | from 1a) | 48% |
| | | from 1b) | 86% |
| | | from 1c) | 73% (in n-propanol) |

Example 3

Continuous hydrogenation of athe crude discharge from 1e)

Hydrogenation of the crude discharge from Example 1e) is carried out in a 0.3 l tubular reactor containing a fixed bed catalyst with circulating liquid. The reactor is heated to the reaction temperature by an external electrical heating jacket. The gaseous and liquid starting materials flow upward through the reactor. The discharge from the hydrogenation is decompressed and its gaseous and liquid constituents are separated in a gas/liquid separator. Some of the liquid obtained in the separator is returned to the reactor, and the remainder is discharged. The ratio of feed to circulating liquid is 1:10. The catalyst is employed in the form of 2–4 mm pellets or as chips and is activated with hydrogen before the hydrogenation. The methanolic feed contains from 11 to 23% of 1,3-dimethyl-4,5-dihydroxy-imidazolidone.

Table 2 shows the reaction conditions and the selectivity and conversion.

TABLE 2

| Batch No. | Catalyst | Pressure [bar] | Temperature [° C.] | Space velocity [kg/1*h] | Conversion [GC % area] | Selectivity [GC % area] |
|---|---|---|---|---|---|---|
| 1 | 10.4% Ni; 10.2% Co; 4.2% Cu on $Al_2O_3$ | 166 | 175 | 0.018 | 90 | 80 |

We claim:

1. A process for preparing a compound of the formula I

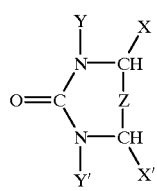

(I)

where

X and X' are, independently of one another, hydrogen, straight-chain or branched $C_1$–$C_4$-alkyl, $C_3$–$C_{12}$-cycloalkyl, or unsubstituted or $C_1$–$C_4$-alkyl-substituted $C_6$–$C_{10}$-aryl;

Y and Y' are, independently of one another, hydrogen, straight-chain or branched $C_1$–$C_4$-alkyl, $C_3$–$C_{12}$-cycloalkyl, or unsubstituted or $C_1$–$C_4$-alkyl-substituted $C_6$–$C_{10}$-aryl, and Z is a single bond or an unsubstituted or X- or X'-substituted $C_1$–$C_4$-alkylene radical, which comprises a) reacting a compound of the formula II

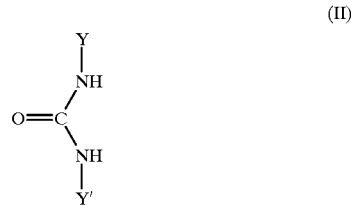

(II)

where Y and Y' have the abovementioned meanings, with a compound of the formula III

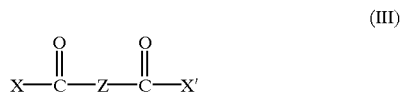

(III)

where X, X' and Z have the abovementioned meanings, and b) hydrogenating the product from step a) in the presence of a metal-containing catalyst.

2. A process as defined in claim 1, wherein step a) is carried out in aqueous or aqueous/organic solvent.

3. A process as defined in claim 1, wherein step a) is carried out in an aqueous/organic solvent which contains about 1–80% by weight, in particular about 30–60% by weight, of organic solvent based on the precursor mixture.

4. A process as defined in claim 1, wherein step a) is followed by removal of the solvent, and the residue being taken up in an organic solvent and hydrogenated.

5. A process as defined in claim 2, wherein the reaction mixture from step a) is hydrogenated were appropriate after further addition of organic solvent.

6. A process as defined in claim 1, wherein step a) results in cyclic urea derivatives of the formulae IV, V or VI

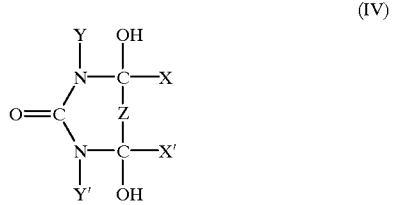

(IV)

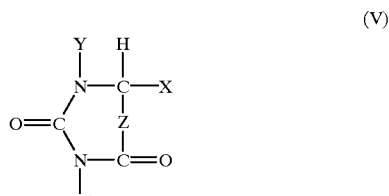

(V)

-continued

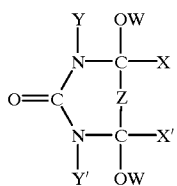
(VI)

where X, X', Y, Y' and Z have the abovementioned meanings, and W is a straight-chain or branched $C_1$–$C_4$-alkyl radical, or mixtures thereof.

7. A process as defined in claim 2, wherein a $C_1$–$C_6$-alkanol, a $C_1$–$C_5$-carboxylic acid, an ester of a $C_1$–$C_3$-carboxylic acid with a $C_1$–$C_3$-alkanol or a linear or cyclic ether with 3 to 6 ring members is employed as organic solvent.

8. A process as defined in claim 4, wherein a $C_1$–$C_6$-alkanol, a $C_1$–$C_5$-carboxylic acid, an ester of a $C_1$–$C_3$-carboxylic acid with a $C_1$–$C_3$-alkanol or a linear or cyclic ether with 3 to 6 ring members is employed as organic solvent.

9. A process as defined in claim 1, wherein step a) is carried out at a pH in the range from 3 to 14.

10. A process as defined in claim 1, wherein step b) is carried out at about 130–300° C.

11. A process as defined in claim 1, wherein step b) is carried out under a pressure of about 130–320 bar.

12. A process as defined in claim 1, wherein the compounds of the formulae II and III are employed in the molar ratio of about 1:1.5 to about 1.5:1.

13. A process as defined in claim 1, wherein the metal-containing catalyst is employed in an amount of about 1–30% of the weight of the product from step a).

* * * * *

UNITED STATES PATENT AND TRADEMARK OFFICE
CERTIFICATE OF CORRECTION

PATENT NO.: 6,103,898

DATED: August 15, 2000

INVENTOR(S): KRAMER et al.

It is certified that error appears in the above-identified patent and that said Letters Patent is hereby corrected as shown below:

Col. 2, line 48, "position a" should be --position $\alpha$--.

Col. 7, line 22, "athe" should be --the--.

Col. 10, claim 8, line 2, "$C_f$-$C_5$-carboxylic" should be --$C_1$-$C_5$-carboxylic--.

Signed and Sealed this

Twenty-ninth Day of May, 2001

*Attest:*

NICHOLAS P. GODICI

*Attesting Officer*     *Acting Director of the United States Patent and Trademark Office*